United States Patent
Long et al.

(10) Patent No.: US 6,187,002 B1
(45) Date of Patent: Feb. 13, 2001

(54) CAPACITIVE ELECTROSURGICAL TROCAR INCLUDING ADAPATER

(75) Inventors: Gary L. Long, Cincinnati; Lynetta J. Freeman, West Chester; Bryan D. Knodel, Cincinnati, all of OH (US)

(73) Assignee: Ethicon Endo-Surgery, Inc., Cincinnati, OH (US)

( * ) Notice: Under 35 U.S.C. 154(b), the term of this patent shall be extended for 0 days.

(21) Appl. No.: 09/256,611

(22) Filed: Feb. 23, 1999

Related U.S. Application Data

(62) Division of application No. 08/885,458, filed on Jun. 30, 1997.

(51) Int. Cl.[7] .................................................. A61B 17/36
(52) U.S. Cl. ................... 606/46; 606/48; 606/50; 606/52; 604/164.01; 604/165.01; 604/272
(58) Field of Search .................. 606/41, 48, 50, 606/45, 46, 51, 52, 170, 185, 32–34; 604/164–167, 204, 272, 164.01, 165.01

(56) References Cited

U.S. PATENT DOCUMENTS

| | | |
|---|---|---|
| 1,620,929 | 3/1927 | Wallerich . |
| 4,535,773 | 8/1985 | Yoon ..................... 604/51 |
| 4,674,010 | 6/1987 | Van den Steen ..................... 361/433 |
| 4,717,438 | 1/1988 | Benge et al. ......................... 156/152 |
| 4,799,480 | 1/1989 | Abraham et al. ............... 128/303.13 |
| 4,825,217 | 4/1989 | Choi ..................... 343/135 |
| 4,884,982 | 12/1989 | Fleming et al. ..................... 438/620 |
| 4,934,960 | 6/1990 | Capp et al. .......................... 439/620 |
| 4,936,842 | 6/1990 | D'Amelio et al. ..................... 606/42 |
| 5,105,829 | 4/1992 | Fabian et al. ......................... 128/899 |
| 5,124,509 | 6/1992 | Hoendervoogt et al. ............... 178/19 |
| 5,207,691 | 5/1993 | Nardella ................. 606/142 |
| 5,273,524 | 12/1993 | Fox et al. ..................... 604/21 |
| 5,342,356 | 8/1994 | Ellman et al. .......................... 606/32 |
| 5,342,357 | 8/1994 | Ellman et al. .......................... 606/32 |
| 5,344,420 | 9/1994 | Hilal et al. .............................. 606/28 |
| 5,354,291 | 10/1994 | Bales et al. ............................ 604/35 |
| 5,380,321 | 1/1995 | Yoon ..................................... 606/41 |
| 5,383,860 | 1/1995 | Lau ..................................... 604/167 |
| 5,387,196 | 2/1995 | Smith et al. ......................... 604/164 |
| 5,387,197 | 2/1995 | Green et al. ......................... 604/158 |
| 5,391,166 | 2/1995 | Eggers .................................. 606/48 |
| 5,403,312 | 4/1995 | Yates et al. ............................ 606/50 |
| 5,417,687 | 5/1995 | Nardella et al. ....................... 606/32 |
| 5,432,486 | 7/1995 | Wong .................................. 333/109 |
| 5,437,277 | 8/1995 | Dumoulin et al. ................ 128/652.1 |
| 5,443,462 | 8/1995 | Hannant ................................. 606/34 |
| 5,445,142 | 8/1995 | Hassler, Jr. .......................... 600/105 |
| 5,445,638 | 8/1995 | Rydell et al. .......................... 606/51 |
| 5,540,684 | 7/1996 | Hassler, Jr. ............................. 606/40 |
| 5,545,142 | 8/1996 | Stephens et al. ..................... 604/167 |

(List continued on next page.)

FOREIGN PATENT DOCUMENTS 37 08 8801
   A1     3/1987  (DE) .

* cited by examiner

Primary Examiner—Linda C. M. Dvorak
Assistant Examiner—David M. Ruddy

(57) ABSTRACT

In the present invention, a surgical trocar is adapted to capacitively couple electrosurgical energy to specially adapted cordless electrosurgical instruments. In one embodiment of the present invention, an electrosurgical trocar includes a cannula, a capacitive electrosurgical adapter and a locking connector adapted to connect the cannula to the capacitive electrosurgical adapter. The cannula is an elongated tube which may be inserted into a body cavity, duct or vessel. The electrosurgical adapter includes a housing with an elongated central aperture, an adapter proximal capacitor plate and an adapter distal capacitor plate positioned in and extending axially along the elongated aperture, first and second electrical conductors, first and second external conductors, a compression mechanism, an outer housing and an electrical cord.

2 Claims, 11 Drawing Sheets

U.S. PATENT DOCUMENTS

| | | |
|---|---|---|
| 5,562,611 | 10/1996 | Transue .................................. 604/26 |
| 5,591,192 | 1/1997 | Privitera et al. ..................... 606/185 |
| 5,597,107 | 1/1997 | Knodel et al. .................... 227/175.2 |
| 5,599,348 | 2/1997 | Gentelia et al. ....................... 604/35 |
| 5,658,279 | 8/1997 | Nardella et al. ...................... 606/45 |
| 5,688,269 * | 11/1997 | Newton et al. ....................... 606/46 |
| 5,733,323 | 3/1998 | Buck et al. ......................... 607/122 |
| 5,772,660 * | 6/1998 | Young et al. ......................... 606/42 |
| 5,792,112 * | 8/1998 | Hart et al. ........................... 604/167 |
| 5,792,141 * | 8/1998 | Logeman .............................. 606/46 |
| 5,925,041 * | 7/1999 | Long et al. ........................... 606/41 |
| 5,961,514 * | 10/1999 | Long et al. ........................... 606/41 |
| 5,984,921 * | 11/1999 | Long et al. ........................... 606/48 |

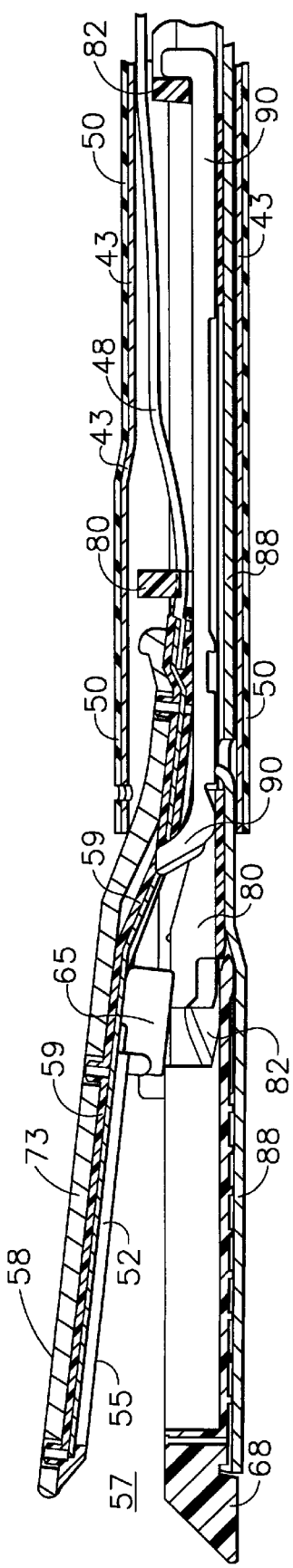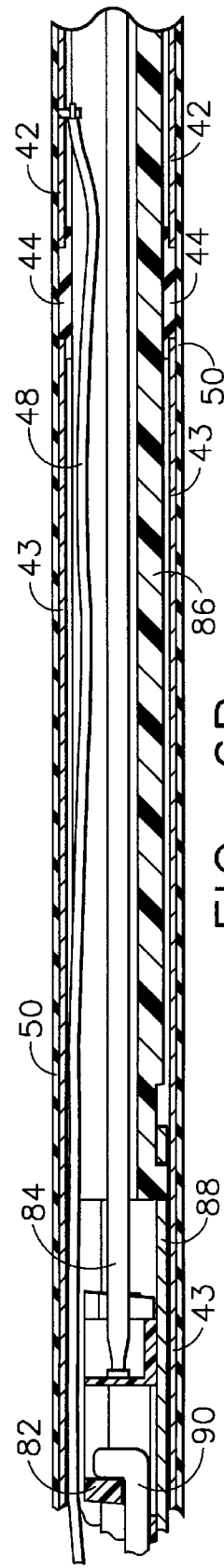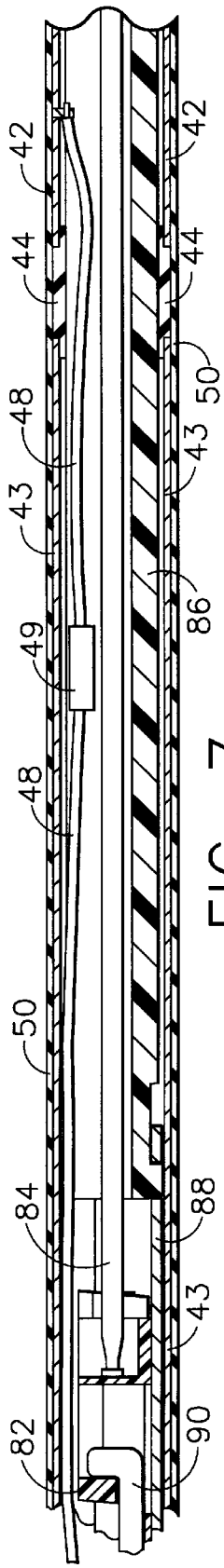

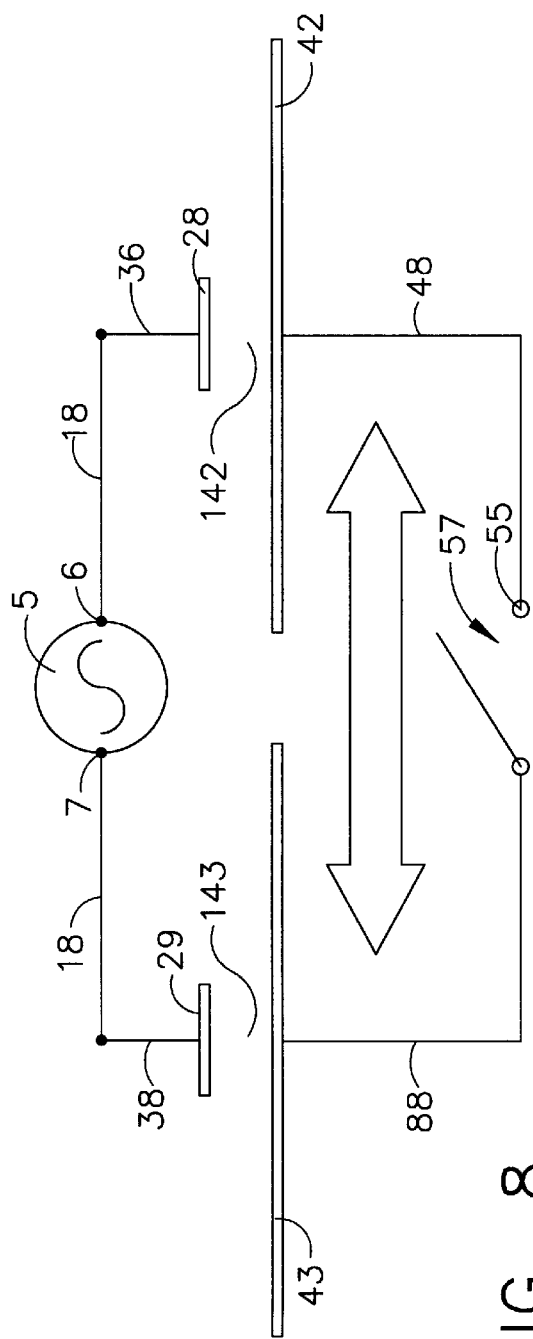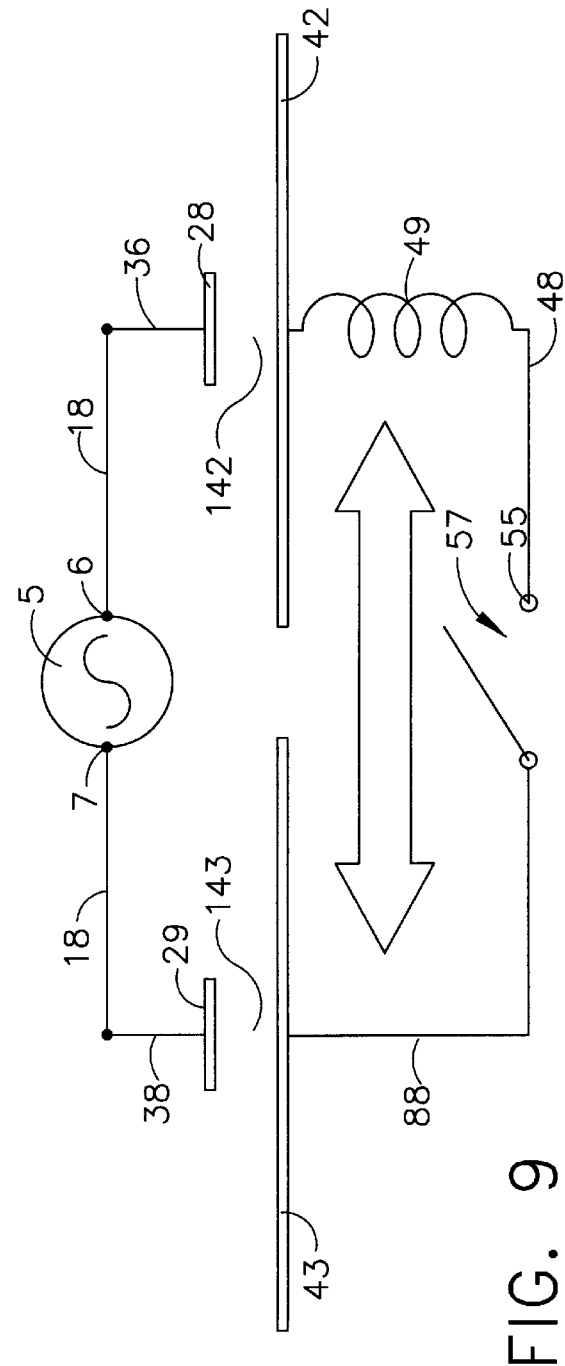

CAPACITIVE ELECTROSURGICAL TROCAR INCLUDING ADAPATER

This is a divisional application of U.S. Ser. No. 08/885,458, filed Jun. 30, 1997. This application is related to the following copending applications: application Ser. No. 08/856,534, filed May 14, 1997; application Ser. No. 08/877,715, filed Jun. 18, 1997; application Ser. No. 08/878,421, filed Jun. 18, 1997; application Ser. No. 08/884,949, filed Jun. 30, 1997; application Ser. No. 08/885,166, filed Jun. 30, 1997; and application Ser. No. 08/885,517, filed Jun. 30, 1997, which applications are hereby incorporated herein by reference.

FIELD OF THE INVENTION

The present invention relates, in general, to an improved electrosurgical trocar and method of use and, more particularly, to an electrosurgical trocar adapted to capacitively couple electrosurgical energy to specially adapted cordless electrosurgical instruments.

BACKGROUND OF THE INVENTION

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. Once the puncture is made, the obturator is withdrawn from the cannula. The cannula then provides a small diameter passageway into and through the body wall to provide access for additional surgical instrumentation to the surgical site. The function, structure and operation of a typical trocar is described in detail in U.S. Pat. No. 5,387,197, which is hereby incorporated herein by reference.

Such additional surgical instruments may include, for example, bipolar or monopolar electrosurgical instruments which utilize radio frequency electrosurgical energy. Known electrosurgical instruments include, for example, bipolar forceps, bipolar scissors, monopolar-hooks, monopolar-scissors and, bipolar endocutters. Each of those instruments has an electrosurgical end effector which is adapted to treat tissue through the application of electrosurgical (e.g. radio frequency or RF) energy to tissue which is brought in contact with the electrosurgical end effector. Most known electrosurgical instruments are connected by electrical cords to electrosurgical generators. The structure and operation of a typical bipolar cutter/stapler ("bipolar endocutter") is described in U.S. Pat. No. 5,403,312 which is hereby incorporated herein by reference.

Electrosurgical generators, such as the Force II generator (which is available from Valleylab of Bolder Colo.), supply electrical energy to the electrosurgical instruments through electrical cords. The electrical cords, being attached directly to the electrosurgical instrument, may make the electrosurgical instrument inconvenient to use. Alternatively, electrical cords may cause undesirable delays as one electrosurgical instrument is unplugged from the generator and another is plugged in. Thus, it would be advantageous to design a cordless electrosurgical instrument. However, such a cordless electrosurgical instrument would have to be connected to the electrosurgical generator through some alternate arrangement. Therefore, it would also be advantageous to design a trocar or a trocar adapter which is adapted to capacitively couple electrosurgical energy to specially designed cordless electrosurgical instruments. It would further be advantageous to design an electrosurgical instrument and electrosurgical trocar or trocar adapter wherein the electrosurgical energy is capacitively coupled from the electrosurgical trocar to the electrosurgical instrument when electrosurgical energy is applied to the electrosurgical trocar or trocar adapter.

SUMMARY OF THE INVENTION

In the present invention, a surgical trocar is adapted to capacitively couple electrosurgical energy to specially adapted cordless electrosurgical instruments. In one embodiment of the present invention, an electrosurgical trocar includes a cannula, a capacitive electrosurgical adapter and a locking connector adapted to connect the cannula to the capacitive electrosurgical adapter. The cannula is an elongated tube which may be inserted into a body cavity, duct or vessel. The electrosurgical adapter includes a housing with an elongated central aperture, a proximal capacitor plate and a distal capacitor plate positioned in and extending axially along the elongated aperture, first and second electrical conductors, first and second external conductors, a compression mechanism, an outer housing and an electrical cord.

In a further embodiment of the present invention, the adapter aperture is formed by an aperture wall positioned in the adapter housing. The adapter proximal and distal capacitor plates are positioned in and extend axially along the aperture, forming at least a portion of the walls of the aperture. The first and second electrical conductors connect the adapter proximal and adapter distal capacitor plates to the first and second external connectors. The compression mechanism biases the adapter proximal and adapter distal capacitor plates toward the center of the adapter aperture. An electrical cord is connected to the first and second external connectors such that the electrical cord may be used to plug the adapter into a suitable electrosurgical generator.

In a further embodiment of the present invention, the adapter proximal capacitor plate is positioned in and substantially surrounds a first portion of the adapter aperture. The adapter distal capacitor plate is positioned in and substantially surrounds the a second portion of the adapter aperture distal to the portion of the aperture substantially surrounded by the adapter proximal capacitor plate. The adapter proximal capacitor plate and the adapter distal capacitor plate are electrically isolated and are separated by an insulation region which substantially surrounds the aperture between the adapter proximal capacitor plate and the adapter distal capacitor plate. The proximal capacitor plate and the distal capacitor plate may be separated from the aperture by a region of dielectric material.

In a further embodiment of the present invention, the adapter proximal capacitor plate is divided into at least a first proximal stator plate and a second proximal stator plate. The proximal stator plates being electrically connected such that the proximal stator plates are electrically common. The adapter distal capacitor plate is divided into at least a first distal stator plate and a second distal stator plate. The distal stator plates being electrically connected such that the distal stator plates are electrically common. In a further embodiment of the present invention, the compression member includes one or more compression rings positioned around the proximal stator plates and one or more compression rings positioned around the distal stator plates. In a further embodiment of the present invention, the stator plates are separated from the aperture by a dielectric region which is adapted to insulate the stator plates and to enhance capacitive of the stator plates to an electrosurgical instrument inserted into the adapter.

In a further embodiment of the present invention, the electrosurgical trocar includes a locking connector which connects the cannula to the capacitive electrosurgical adapter. In this embodiment of the invention, the adapter includes first and second locking cleats extending from the distal end of the connector. The cannula includes receptors such as indentations or ribs which hold the distal ends of the locking cleats in place, thus holding the connector in contact with the cannula. In a further embodiment of the present invention, the capacitive electrosurgical adapter is integrated into and made a part of the trocar cannula.

In a further embodiment of the present invention, each of the capacitor plates comprises an electrically conductive plate covered by a layer of high dielecteric material. The high dielectric material may be composed, at least in part, of a durable high dielectric material such as Barium Titanate (BaTiO$_3$) or other suitable material.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6A is a cutaway view of the end effector of the capacitive electrosurgical instrument illustrated in FIG. 5.

FIG. 6B is a cutaway view of a portion of the closure tube of the capacitive electrosurgical instrument illustrated in FIG. 5.

FIG. 7 is a cutaway view of an alternative embodiment of a portion of the closure tube of the capacitive electrosurgical instrument illustrated in FIG. 5.

FIG. 8 is a schematic diagram graphically illustrating the capacitive coupling between a capacitive electrosurgical trocar or trocar adapter and a capacitive electrosurgical instrument according to the present invention.

FIG. 9 is a schematic diagram graphically illustrating the capacitive coupling between a capacitive electrosurgical trocar or trocar adapter and an alternative embodiment of a capacitive electrosurgical instrument.

DETAILED DESCRIPTION OF THE INVENTION

Figure 1:
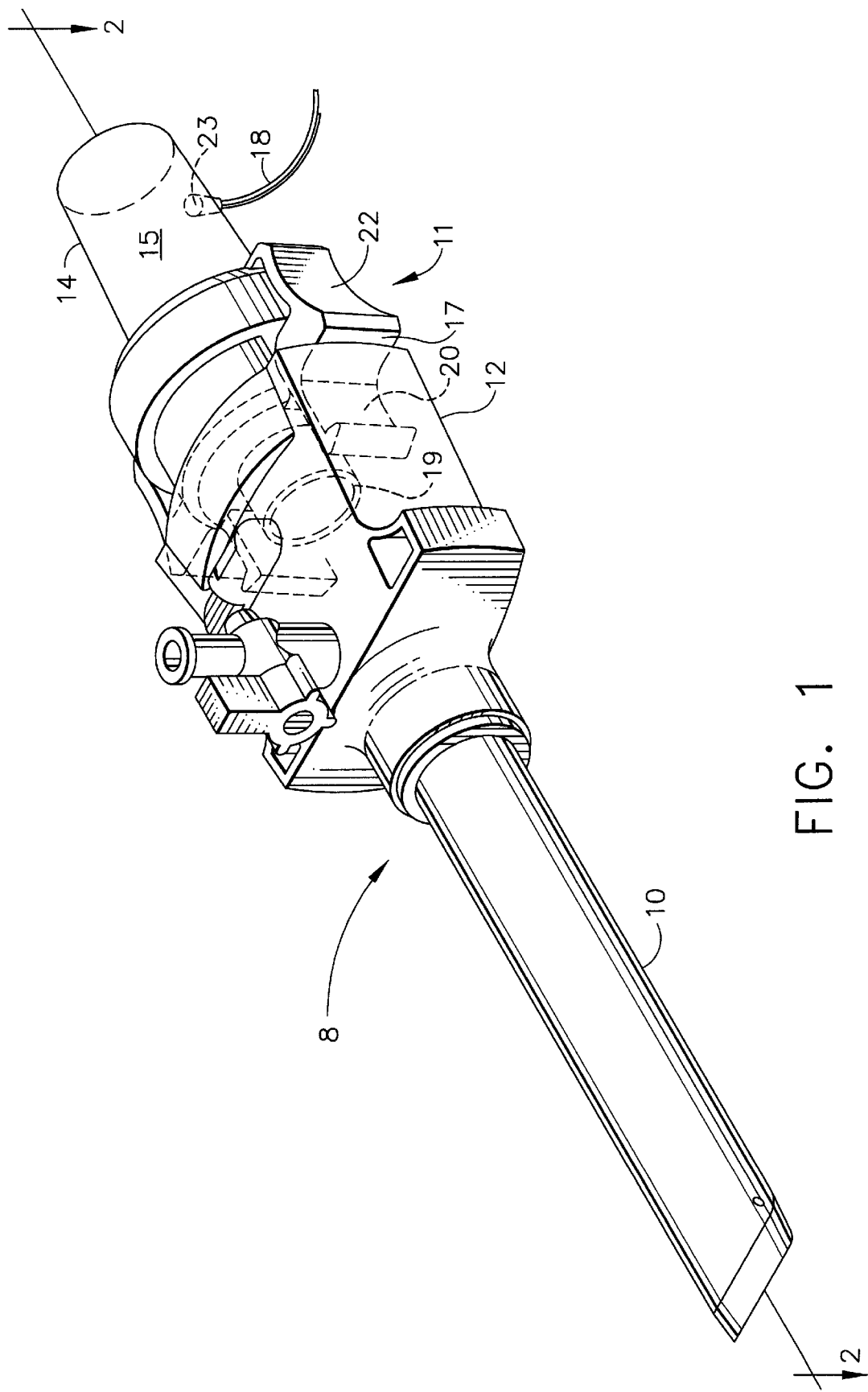
FIG. 1 is a perspective view of a capacitive electrosurgical trocar according to the present invention.
Figure 1A:
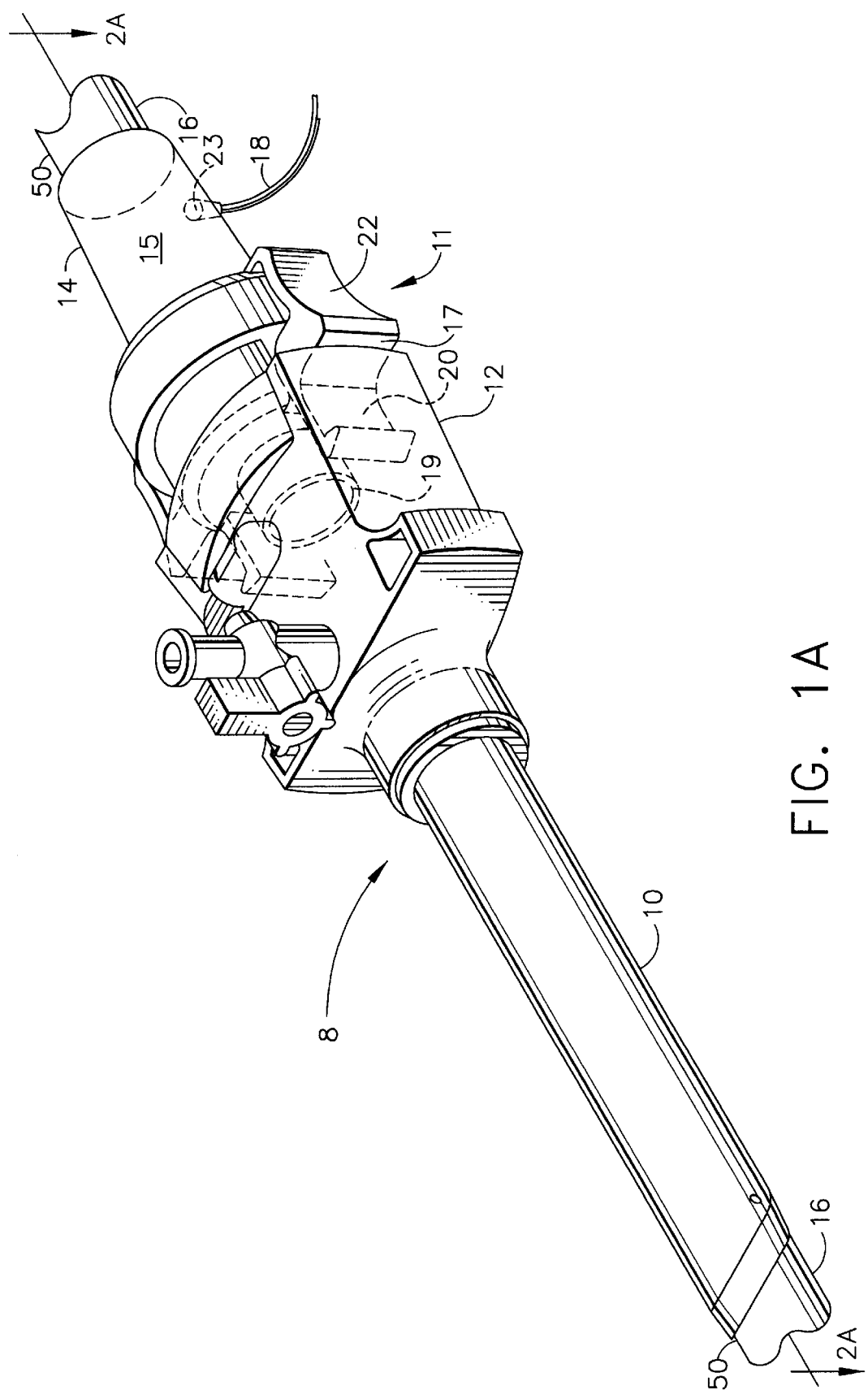
FIG. 1A is a perspective view of a capacitive electrosurgical trocar according to the present invention including a portion of the closure tube of a capacitive electrosurgical instrument shown positioned in the central aperture of the capacitive electrosurgical trocar.

FIG. 1 is a perspective view of a capacitive electrosurgical trocar 11 according to the present invention. FIG. 1A is a perspective view of capacitive electrosurgical trocar 11 including a portion of closure tube 50 of capacitive electrosurgical instrument 16. Capacitive electrosurgical trocar 11 includes trocar cannula 8 and a capacitive electrosurgical adapter 14. Capacitive electrosurgical trocar 11 may also include an obturator assembly (not shown) such as the one illustrated in U.S. Pat. No. 5,387,197, which has been previously incorporated herein by reference. Trocar cannula 8 includes cannula housing 12 and cannula tube 10, extending from cannula housing 12. Capacitive electrosurgical adapter 14 includes an adapter housing 15, locking connector 17 and an electric cord 18. In the embodiment of the invention illustrated in FIG. 1, capacitive electrosurgical adapter 14 is connected to trocar cannula 8 by locking connector 17. Locking connector 17 includes locking cleats 20 and release buttons 22. It will be apparent that capacitive electrosurgical adapter 14 may be integrated directly into trocar cannula housing 12, thus eliminating the need for locking connector 17.

Figure 2:
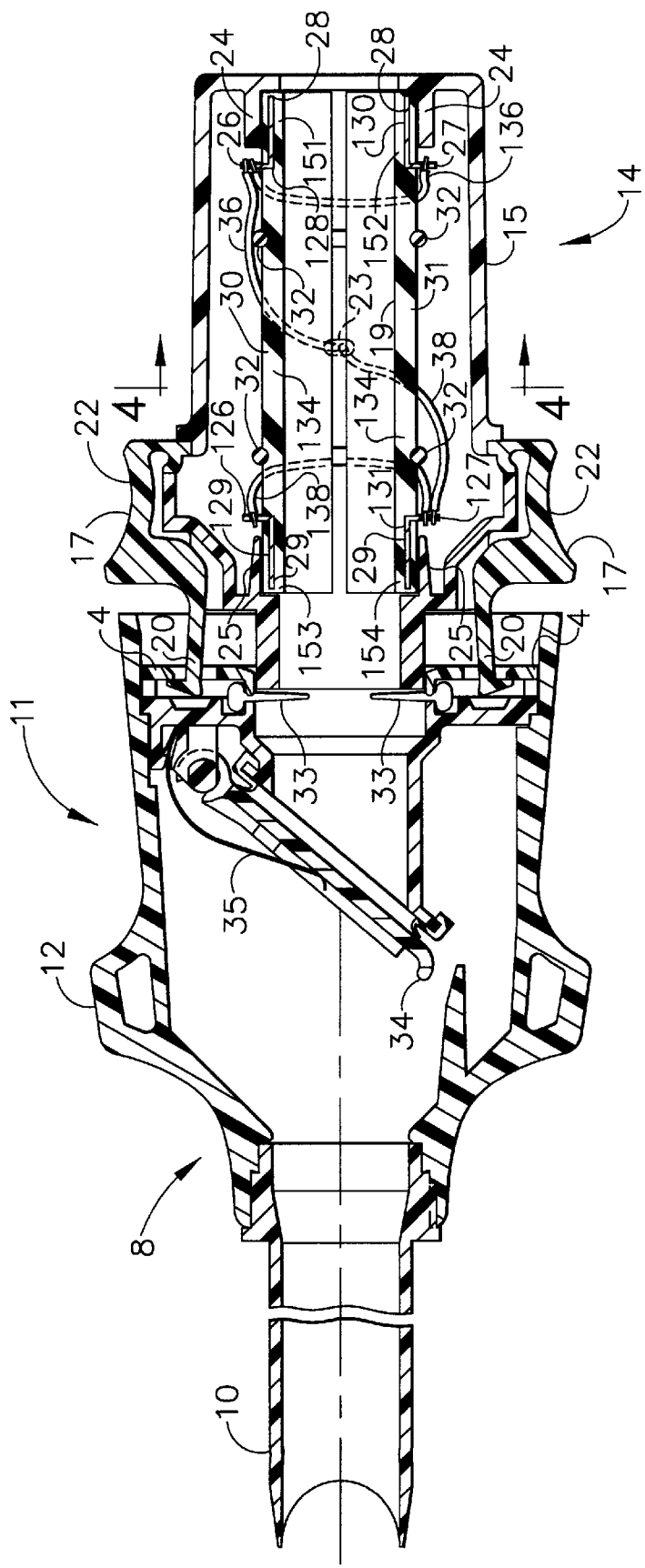
FIG. 2 is a plan view section taken along 2—2 in FIG. 1 through the capacitive electrosurgical trocar illustrated in FIG. 1.
Figure 2A:
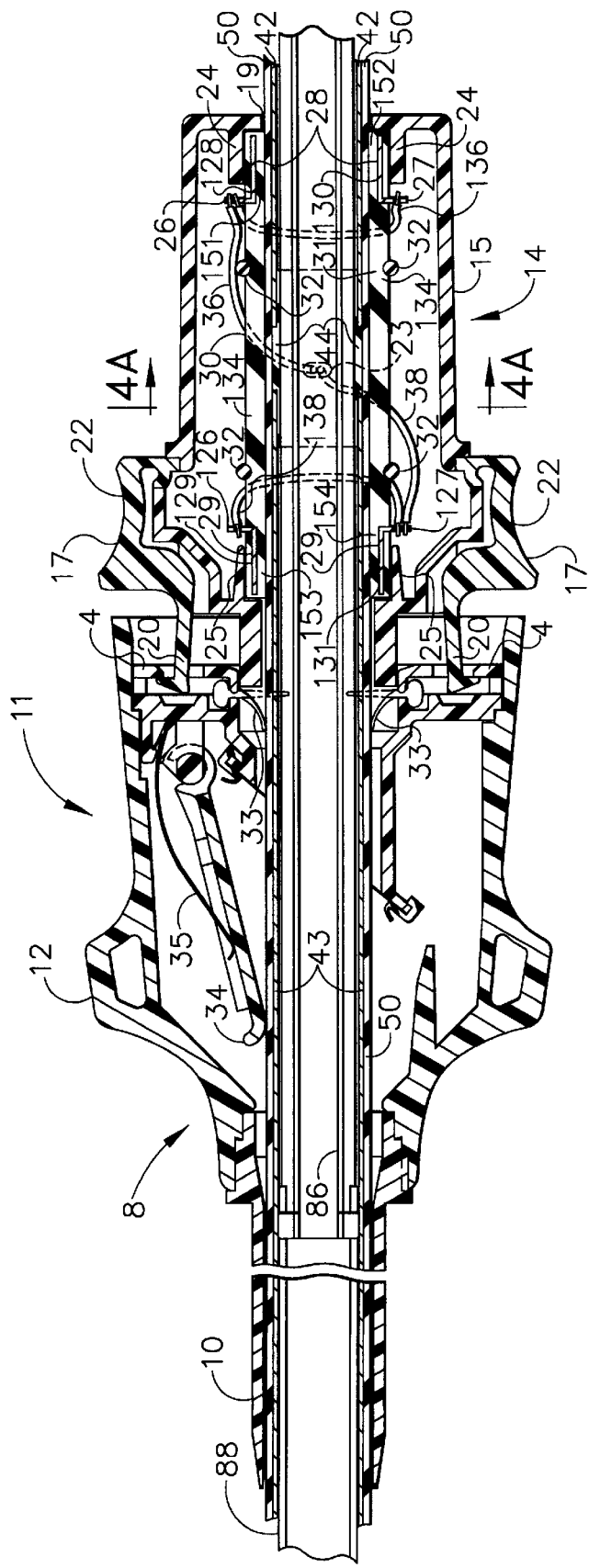
FIG. 2A is a plan view section taken along 2A—2A in FIG. 1A through the capacitive electrosurgical trocar and closure tube illustrated in FIG. 1A.

FIG. 2 is a plan view section taken along 2—2 in FIG. 1 through capacitive electrosurgical trocar 11. FIG. 2A is a plan view section taken along 2A—2A in FIG. 1A through capacitive electrosurgical trocar 11 and a portion of closure tube 50 of capacitive electrosurgical instrument 16. In FIGS. 2 and 2A, cannula housing 12 includes flapper valve 34, valve spring 35 and ring gasket 33. Capacitive electrosurgical adapter 14 includes central aperture 19, front flange 25 and base flange 24. Central aperture 19 is an elongated aperture for receiving working instruments such as endoscopic electrosurgical instruments. Capacitive electrosurgical adapter 14 further includes a plurality of capacitor plates which, in the embodiment illustrated in FIGS. 2–4, comprise proximal capacitor plate 28 and distal capacitor plate 29. At least a portion of the interior wall of central aperture 19 is formed by upper insulator 30 and lower insulator 31. Upper insulator 30 and lower insulator 31 together comprise trocar insulator 134. Upper insulator 30 and lower insulator 31 are positioned against front flange 25 and base flange 24. Compression member 32 is, in the present embodiment, an o-ring which is positioned outside of upper insulator 30 and lower insulator 31 to bias upper insulator 30 and lower insulator 31 toward the center of central aperture 19. Compression member 32 may also be, for example, a spring, a flexible sleeve, a plurality of o-rings or any other suitable biasing member. Proximal capacitor plate 28 and distal capacitor plate 29, being positioned in upper insulator 30 and lower insulator 31 in the embodiments of FIGS. 1–4 are likewise biased toward the center of central aperture 19 by compression member 32. Latch detents 4 in cannula housing 12, are adapted to receive locking cleats 20 of locking connector 17.

Figure 3:
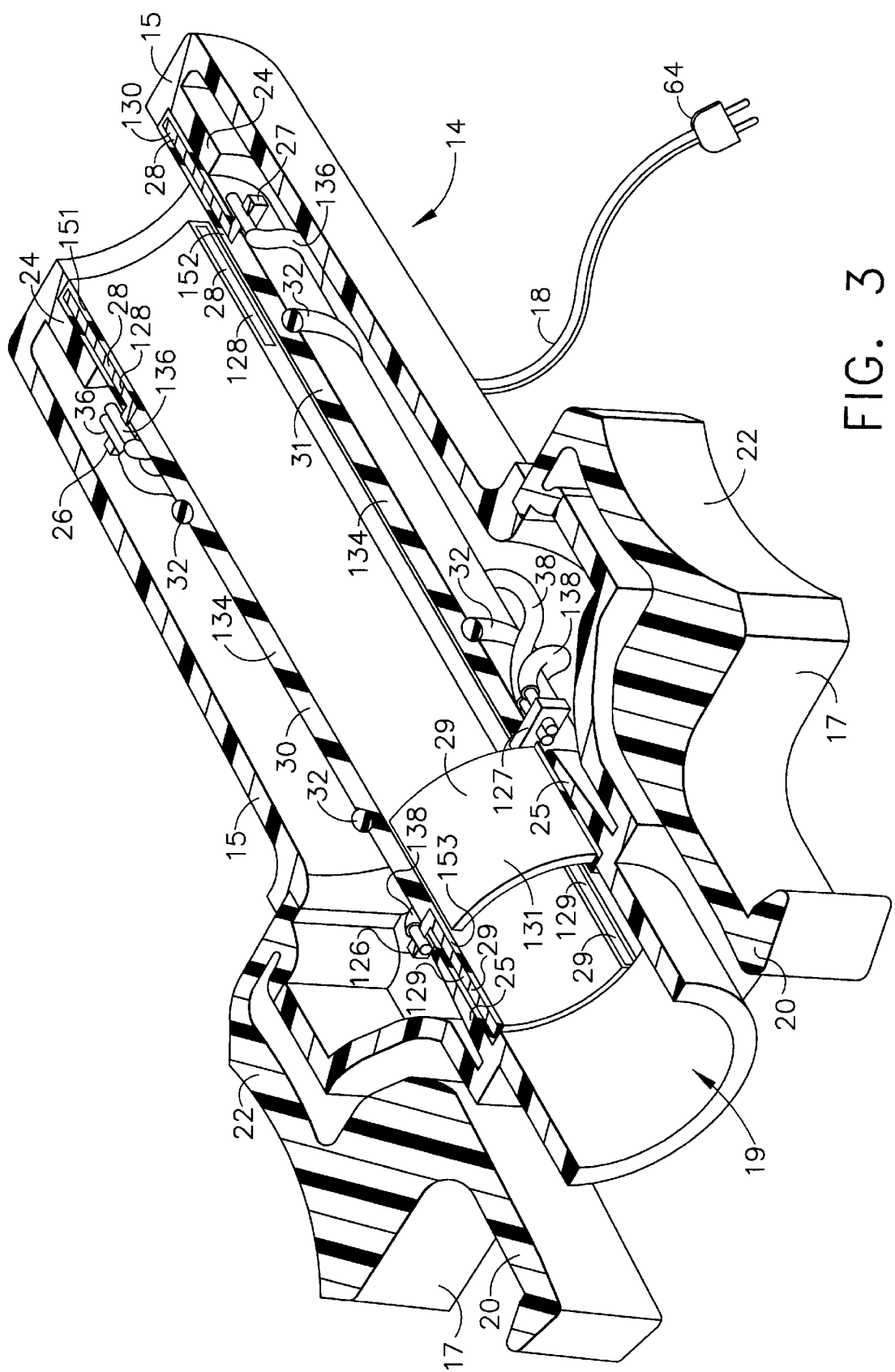
FIG. 3 is a perspective view in plane section of the capacitive electrosurgical adapter illustrated in FIG. 1.
Figure 3A:
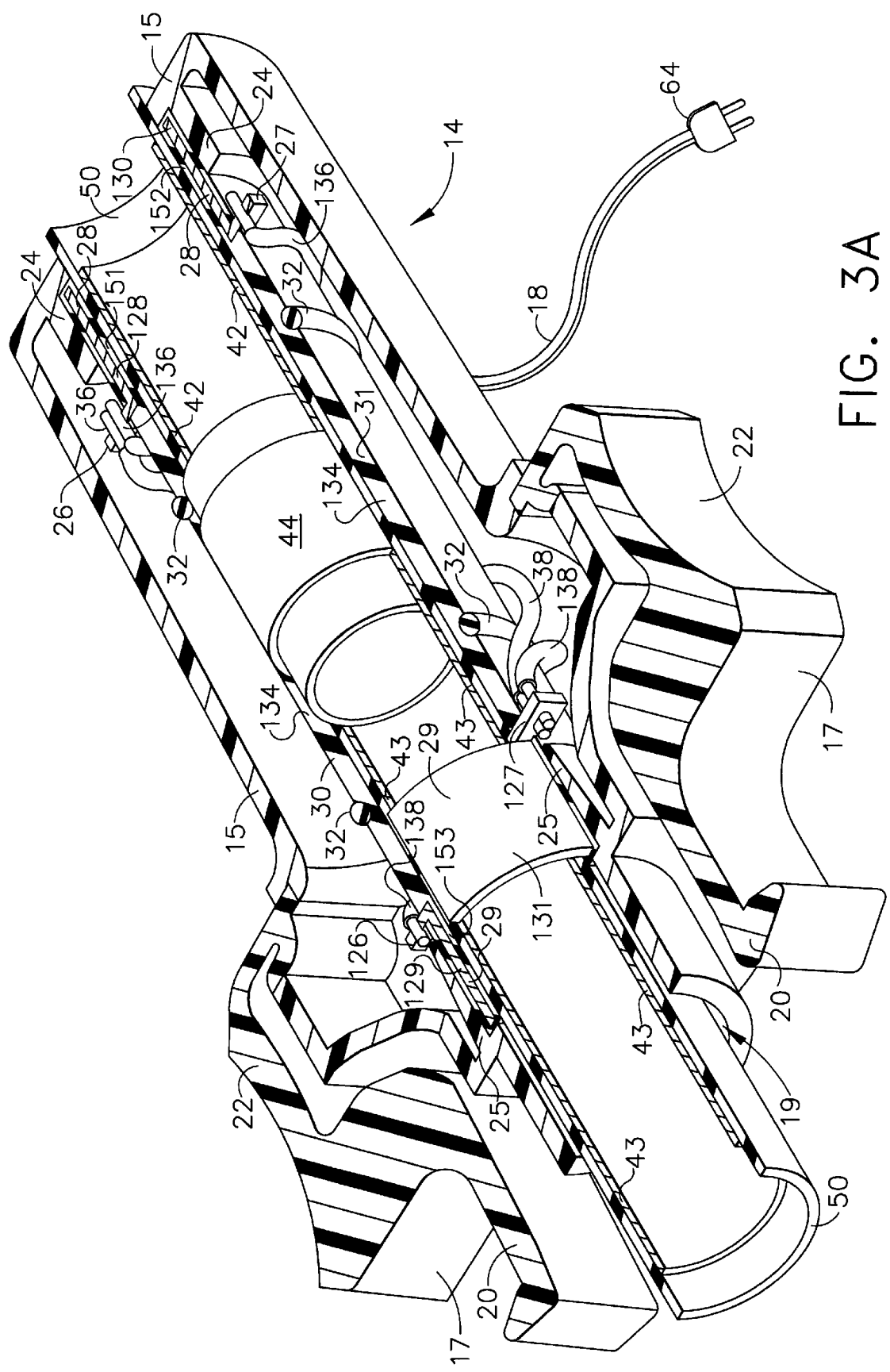
FIG. 3A is a perspective view in plane section of the capacitive electrosurgical adapter and closure tube illustrated in FIG. 1A.

FIG. 3 is a perspective view in plane section of capacitive electrosurgical adapter 14. FIG. 3A is a perspective view in plane section of capacitive electrosurgical adapter 14 and a portion of closure tube 50 of electrosurgical instrument 16. Referring now to FIGS. 2–4 and 2A–4A and particularly to FIGS. 3 and 3A, capacitive electrosurgical adapter 14 includes adapter housing 15, locking cleats 20, base flange 24, front flange 25 and release buttons 22. Upper insulator 30 and lower insulator 31 are positioned in capacitive electrosurgical adapter 14 and are held in place by base flange 24 and front flange 25. Compression members 32 bias upper insulator 30 and lower insulator 31 toward the center of central aperture 19. Upper insulator 30 and lower insulator 31 are preferably constructed of a high dielectric material such as Barium Titanate ($BaTiO_3$). Proximal capacitor plate 28 comprises first proximal capacitor stator plate 128 and second proximal capacitor stator plate 130. Distal capacitor plate 29 comprises first distal capacitor stator plate 129 and second distal capacitor stator plate 131. Electrosurgical energy is supplied to capacitive electrosurgical trocar 11 by electric cord 18 which is connected to bipolar electrosurgical plug 64. Electric cord 18 is electrically connected to upper conductor 36 and lower conductor 38. Upper conductor 36 is electrically connected to upper stator tab 26 which is electrically connected to first proximal capacitor stator plate 128. Conductor 136 electrically connects upper stator tab 26 to lower stator tab 27 which is electrically connected to second proximal capacitor stator plate 130. Lower conductor 38 is electrically connected to lower stator tab 127 which is electrically connected to second distal capacitor stator plate 131. Conductor 138 electrically connects lower stator tab 127 to upper stator tab 126 which is electrically connected to first distal capacitor stator plate 129. Thus, electrosurgical energy may be coupled from bipolar electrosurgical plug 64 to each of proximal capacitor plate 28 and distal capacitor plate 29. Proximal capacitor plate 28 and distal capacitor plate 29 are positioned in, and electrically insulated from one another by trocar insulator 134. In particular, first proximal capacitor stator plate 128 and first distal capacitor stator plate 129 are positioned in upper insulator 30 which also insulates first proximal capacitor stator plate 128 from first distal capacitor stator plated 129. Further, second proximal capacitor stator plate 130 and second distal capacitor stator plate 131 are positioned in lower insulator 31 which also insulates second proximal capacitor stator plate 130 from second distal capacitor stator plated 131. Compression member 32 surrounds upper insulator 30 and lower insulator 31. First proximal dielectric region 151 comprises the portion of upper insulator 30 positioned between first proximal capacitor stator plate 128 and central aperture 19. Second proximal dielectric region 152 comprises the portion of lower insulator 31 positioned between second proximal capacitor stator plate 130 and central aperture 19. First distal dielectric region 153 comprises the portion of upper insulator 30 positioned between first distal capacitor stator plate 129 and central aperture 19. Second distal dielectric region 154 comprises the portion of lower insulator 31 positioned between second distal capacitor stator plate 131 and central aperture 19.

Figure 4:
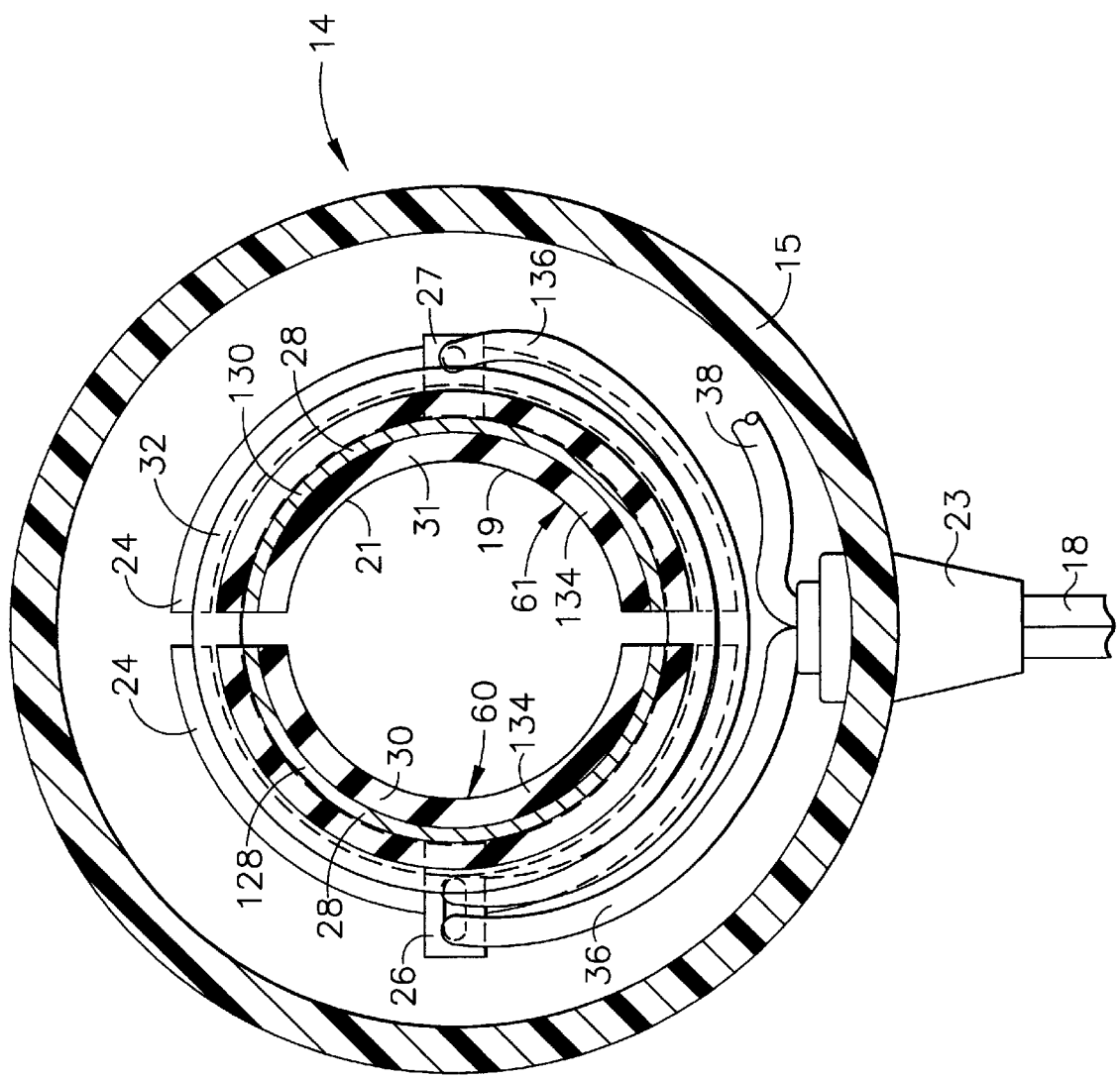
FIG. 4 is a section view taken along line 4—4 of FIG. 2.
Figure 4A:
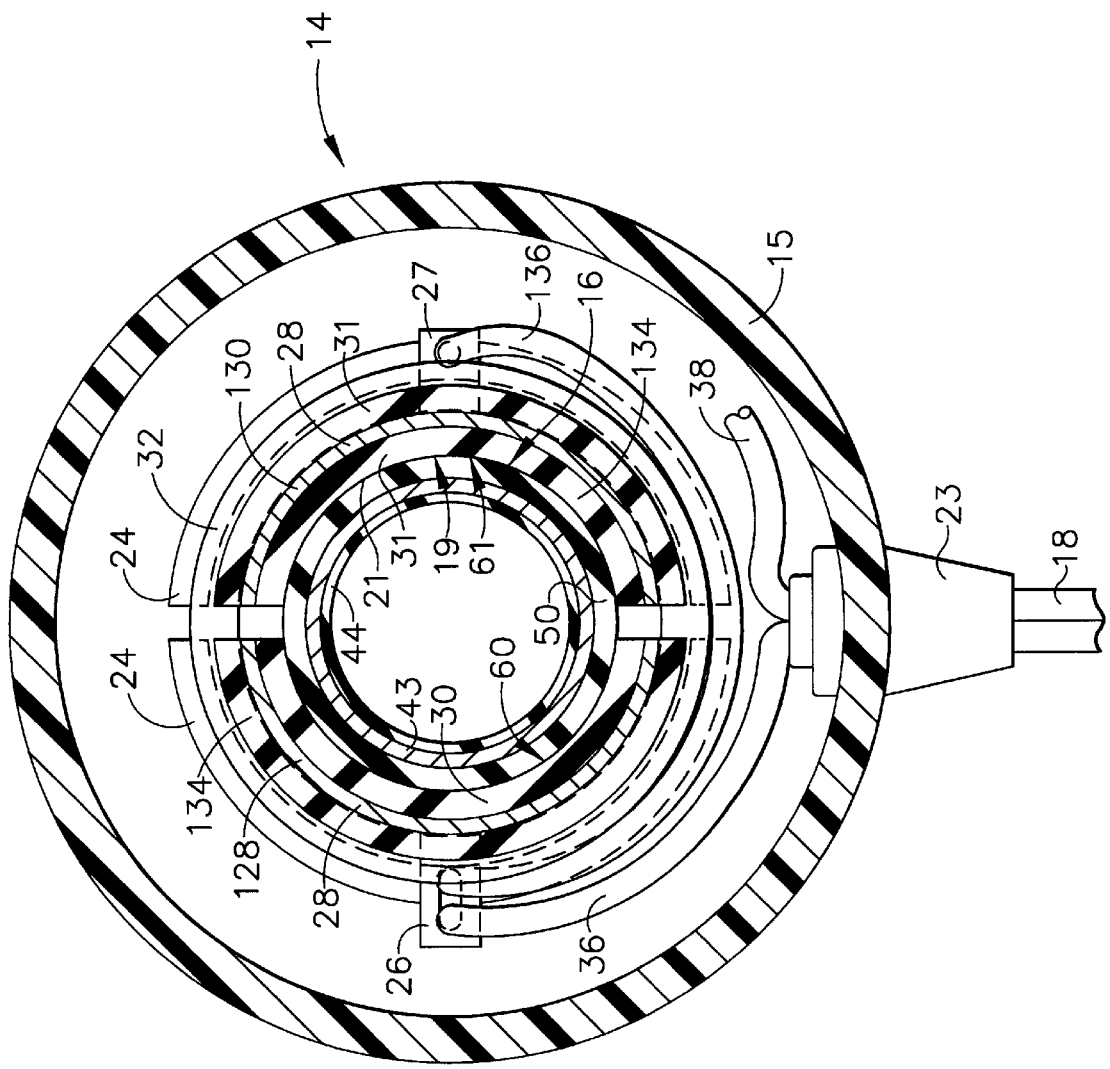
FIG. 4A is a section view taken along line 4A—4A of FIG. 2A.

FIG. 4 is a sectional view of capacitive electrosurgical adapter 14 taken along line 4—4 of FIG. 2. FIG. 4A is a section view of capacitive electrosurgical adapter 14 taken along line 4A—4A of FIG. 2A. Referring now to FIGS. 2–4 and particularly to FIGS. 4 and 4A, central aperture 19 is defined by aperture interior wall 21. The portion of aperture interior wall 21 visible in FIG. 4 is formed, at least in part, by first insulator surface 60 of upper insulator 30 and insulator surface 61 of lower insulator 31. Compression member 32, which comprises two o-rings in the embodiment of FIGS. 2–4, biases upper insulator 30 and lower insulator 31 toward the center of central aperture 19. Electric cord 18 is connected to first proximal capacitor stator plate 128 of proximal capacitor plate 28 by upper conductor 36 and upper stator tab 26. Upper stator tab 26 is connected to lower stator tab 27 by conductor 136. Electric cord 18 is connected to second distal capacitor stator plate 131 of distal capacitor plate 29 by lower conductor 38 and lower stator tab 27. As illustrated particularly in FIGS. 2 and 3, Upper stator tab 126 is connected to lower stator tab 127 by conductor 138. Base flange 24 and front flange 25, which are part of adapter housing 15, hold upper insulator 30 and lower insulator 31 in place, thus positioning proximal capacitor plate 28 and distal capacitor plate 29 around central aperture 19. Strain relief 23 protects electric cord 18 as it passes through adapter housing 15. Although proximal capacitor plate 28 is illustrated as being visible in FIGS. 4 and 4A, it will be apparent that proximal capacitor plate 28 is shown as being visible for convenience in describing the invention and would actually be hidden.

Figure 5:
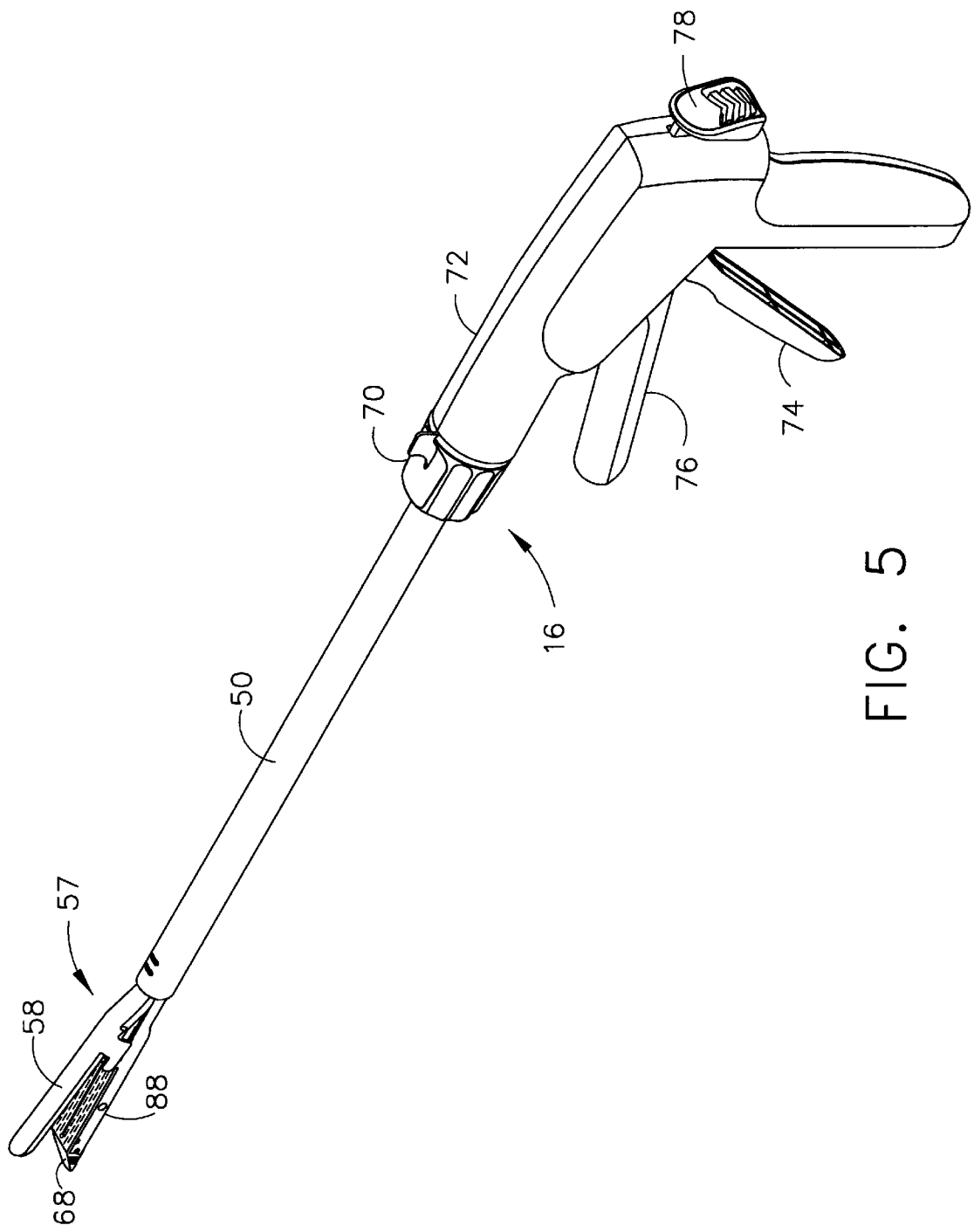
FIG. 5 is a perspective view of a cordless capacitive electrosurgical instrument according to the present invention.

FIG. 5 is a perspective view of a capacitive cordless electrosurgical instrument 16 which may be, for example, a bipolar cutter/stapler. In FIG. 5, capacitive electrosurgical instrument 16 includes handle 72, closure tube 50 and bipolar end effector 57. Closure tube 50 is elongated to facilitate insertion of end effector 57 through a trocar cannula, thus facilitating the use of capacitive electrosurgical instrument 16 in endoscopic or laparoscopic surgical procedures. Handle 72, which is located at the proximal end of capacitive electrosurgical instrument 16, includes grasping trigger 74, firing trigger 76 and release trigger 78. Closure tube 50, which connects handle 72 to end effector 57, includes rotation knob 70. End effector 57, which is located at the distal end of closure tube 50 includes anvil 58, cartridge channel 88 and staple cartridge 68. Capacitive electrosurgical instrument 16 is similar in structure and operation to the bipolar endoscopic electrocautery linear cutting and stapling instrument illustrated and described in U.S. Pat. No. 5,403,312, which has been previously incorporated herein by reference. However capacitive electrosurgical instrument 16 is cordless and electrosurgical energy is capacitively coupled into electrosurgical instrument 16. In captive electrosurgical instrument 16, electrosurgical energy is supplied to instrument 16 through capacitive plates which may be located in closure tube 50.

FIG. 6A is a cutaway view of end effector 57 of capacitive cordless electrosurgical instrument 16. FIG. 6B is a cutaway view of a portion of closure tube 50 of capacitive cordless electrosurgical instrument 16. FIG. 7 is a cutaway view of an alternate embodiment of a portion of closure tube 50 of capacitive cordless electrosurgical instrument 16. In the embodiments of electrosurgical instrument 16 illustrated in FIGS. 6A, 6B and 7, anvil base 73 of Anvil 58 supports electrode assembly 52 and includes anvil guide 65 and staple forming slots (not shown). Electrode assembly 52 is electrically coupled to first electrode conductor 48 and to anvil electrodes 55. Anvil base 73 is insulated from electrode assembly 52 by anvil insulator 59. First electrode conductor 48 is electrically connected to instrument proximal capacitor plate 42. Instrument proximal capacitor plate 42 is positioned in the proximal portion of closure tube 50. Channel 88 of end effector 57 supports staple cartridge 68, wedge guide 80 and wedge block assembly 82. Channel 88 extends into and, being constructed of electrically conductive material, is electrically coupled to instrument distal capacitor plate 43 which is positioned in the distal portion of closure tube 50. Thus, channel 88 may provide a return path for electrical energy coupled to anvil electrodes 55 of end effector 57 when end effector 57 is used to grasp tissue or other electrically conductive material and that electrically conductive material touches both channel 88 and anvil electrodes 55. Electrosurgical energy coupled to channel 88 may be coupled back to electrosurgical trocar 11 through instrument distal capacitor plate 43. Instrument proximal capacitor plate 42 is electrically insulated from Instrument distal capacitor plate 43 by closure tube insulator 44. Closure tube 50 also supports and encloses the proximal end of anvil 58, the proximal end of channel 88, firing rod 84, the proximal end of knife 90, channel retainer 86 and at least a portion of wedge block assembly 82 and wedge guide 80. Closure tube 50 may preferably be constructed of a durable high dielectric insulating material such as, for example, Barium Titanate ($BaTiO_3$). Anvil 58 opens and closes by, for example, pivoting around one or more pivot pins (not shown). In the embodiment illustrated in FIG. 7, matching inductor 49 may be used to improve the efficiency of energy transfer to tissue grasped by end effector 57. The structure and operation of the mechanical features of electrosurgical instrument 16 may be better understood with reference to the mechanical cutting and stapling instrument illustrated and described in U.S. Pat. No. 5,597,107 which is hereby incorporated herein by reference.

FIG. 8 is a schematic diagram graphically illustrating the capacitive coupling between capacitive electrosurgical trocar 11 and capacitive electrosurgical instrument 16. In FIG. 8, Proximal capacitor 142 comprises proximal capacitor plate 28, trocar insulator 134, closure tube 50 and instrument proximal capacitor plate 42. More particularly, proximal capacitor 142 comprises first proximal capacitor stator plate 128, first proximal dielectric region 151, second proximal capacitor stator plate 130, second proximal dielectric region 152, a portion of the proximal end of closure tube 50, and instrument proximal capacitor plate 42. Distal capacitor 143 comprises distal capacitor plate 29, trocar insulator 134, closure tube 50 and instrument distal capacitor plate 43. More particularly, distal capacitor 143 comprises first distal capacitor stator plate 129, first distal dielectric region 153, second distal capacitor stator plate 131, second distal dielectric region 154, a portion of the distal end of closure tube 50 and instrument distal capacitor plate 43.

In FIGS. 8 and 9, first output 6 of electrosurgical generator 5 is connected to proximal capacitor plate 28 of proximal capacitor 142 through cord 18 and upper conductor 36. Second output 7 of electrosurgical generator 5 is connected to distal capacitor plate 29 of distal capacitor 143 through cord 18 and lower conductor 38. When end effector 57 is closed around electrically conductive material such as biological tissue, the electrical circuit from instrument proximal capacitor plate 42 of proximal capacitor 142 to instrument distal capacitor plate 43 of distal capacitor 143 is completed. Thus, with end effector 57 closed around conductive material and electrosurgical generator 5 turned on, electrosurgical energy, such as electrical current at a predetermined output frequency and power, passes from electrosurgical generator 5, through proximal capacitor 142, to end effector 57 and returns through distal capacitor 143 and back to second output 7 of electrosurgical generator 5.

As FIGS. 8 and 9 schematically illustrate, instrument proximal capacitor plate 42 and instrument distal capacitor plate 43 are elongated so that movement of electrosurgical instrument 16 does not result in loss of capacitive coupling in capacitors 142 and 143. Thus, even as the instrument is moved within trocar 11 to facilitate treatment of the patient, capacitive coupling may be maintained. The circuit illustrated in FIG. 9 includes a matching inductor 49 which may be used to electrically match capacitive electrosurgical instrument 16 to capacitive electrosurgical trocar 11 in order to increase the power coupled to the tissue grasped by end effector 57. In particular, inductor 49 would be selected to make the load represented by the trocar, instrument and tissue appear to be substantially resistive at the frequency of interest.

In operation, trocar cannula 8 is used with a conventional trocar orbitor (not shown) to penetrate the wall of a body cavity such as, for example, the abdominal wall of a human being. After the body wall is penetrated, the obturator assembly is withdrawn from trocar cannula 8, and the cannula is used as an access portal for the passage of various endoscopic instruments to provide, for example, access to the internal organs of a human being. Where the endoscopic instrument to be used is a cordless capacitive electrosurgical instrument such as electrosurgical instrument 16, capacitive electrosurgical adapter 14 may be attached to trocar cannula 8. Once capacitive electrosurgical adapter 14 is attached to trocar cannula 8 and electric cord 18 is attached to a suitable electrosurgical generator (such as generator 5 in FIG. 8), capacitive electrosurgical trocar 11 may be used to provide electrosurgical energy to cordless capacitive electrosurgical instruments such as electrosurgical instrument 16. When a cordless capacitive electrosurgical instrument such as electrosurgical instrument 16, is inserted into a body cavity through, for example, capacitive electrosurgical trocar 11, end effector 57 passes through trocar cannula 8 and into the body cavity while most of closure tube 50 remains in trocar 11. Handle 72, which is outside of capacitive electrosurgical trocar 11, may be manipulated by the surgeon to control the position of end effector 57.

A cordless capacitive bipolar electrosurgical instrument according to the present invention, such as electrosurgical instrument 16 of FIG. 5 may be used by inserting the cordless instrument into an appropriate capacitive electrosurgical trocar such as the electrosurgical trocar illustrated in FIG. 1. In the capacitive electrosurgical trocar illustrated in FIG. 1, electrosurgical energy is provided to instrument 16 by, for example, the capacitive coupling between proximal capacitor plate 28 of trocar 11 and instrument proximal capacitor plate 42 of instrument 16. An electrical return path is provided by, for example, the capacitive coupling between distal capacitor plate 29 of trocar 11 and instrument distal capacitor plate 43 of instrument 16. The diameter of central aperture 19 generally corresponds with the outer diameter of closure tube 50 so that closure tube 50 slides through central aperture 19 and the interior of cannula tube 10. Electrical coupling will be maintained so long as capacitor plates 42 and 43 are positioned in central aperture 19 opposite capacitor plates 28 and 29 to form capacitors 142 and 143. Upper insulator 30 and lower insulator 31 form trocar insulator 134. Closure tube 50 and trocar insulator 134, being preferably formed of a material having a high dielectric constant, act as the dielectric for proximal capacitor 142 and distal capacitor 143 which are illustrated schematically in FIG. 8. Compression member 32 helps to ensure that trocar insulator 134 and closure tube 50 maintain good physical contact, minimizing any air gap and enhancing capacitive coupling between the plates of proximal capacitor 142 and the plates of distal capacitor 143. Capacitive electrical coupling may be enhanced by using multiple capacitors in capacitive electrosurgical trocar 11. With instrument capacitor plates 42 and 43 positioned opposite capacitor plates 28 and 29, electrosurgical energy may be supplied to instrument 16 through electric cord 18 and capacitive electrosurgical trocar 11. In the embodiments of the invention illustrated herein, electrosurgical energy supplied to trocar 11 by cord 18 passes through conductors 36, 38, 136 and 138 to stator tabs 26, 126, 27 and 127 and capacitor plates 28 and 29 into electrosurgical instrument 16 via instrument capacitor plates 42 and 43. Electrosurgical energy supplied to electrosurgical instrument 16 via instrument capacitor plates 42 and 43 may be supplied to end effector 57 via the circuit formed by instrument proximal capacitor plate 42, conductor 48, electrode assembly 52, cartridge channel 88 and instrument distal capacitor plate 43. This circuit is completed when biological tissue or other conductive material is grasped by end effector 57, providing a path from electrode assembly 52 to cartridge channel 88. In electrosurgical instrument 16, cartridge channel 88 and anvil electrode 55 are electrically conductive. Thus, where electrode assembly 52 acts as a primary electrode, cartridge channel 88 acts as a secondary or return electrode. When electrically conductive tissue is grasped by end effector 57 and an electrosurgical generator is connected to first instrument proximal capacitor plate 42 and second instrument distal capacitor plate 43, electrosurgical energy will flow through the grasped tissue, coagulating the grasped tissue provided that capacitive electrosurgical instrument 16 is positioned in trocar 11 as described herein. It may also be advantageous to provide one or more switches to control the flow of electrical current to trocar 11 or to end effector 57 of instrument 16.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical trocar, said trocar comprising:
    a) a cannula tube;
    b) a cannula housing connected to said cannula tube; and
    c) a capacitive electrosurgical adapter attached to a proximal end of said cannula housing wherein said trocar includes a locking connector adapted to connect said cannula housing to said adapter.
2. An electrosurgical trocar according to claim 1, wherein said locking connector comprises:
    a) first and second locking cleats extending from a first end of said adapter; and
    b) first and second indentations on said cannula.

* * * * *